United States Patent [19]

Hain et al.

[11] Patent Number: 6,063,988
[45] Date of Patent: May 16, 2000

[54] DNA SEQUENCES ENCODING STILBENE SYNTHASES AND THEIR USE

[75] Inventors: Rüdiger Hain, Langenfeld; Regina Fischer, München, both of Germany

[73] Assignee: Bayer Aktiengesellschaft, Leverkusen, Germany

[21] Appl. No.: 08/836,402

[22] PCT Filed: Oct. 30, 1995

[86] PCT No.: PCT/EP95/04256

§ 371 Date: Sep. 2, 1997

§ 102(e) Date: Sep. 2, 1997

[87] PCT Pub. No.: WO96/15251

PCT Pub. Date: May 23, 1996

[30] Foreign Application Priority Data

Nov. 10, 1994 [DE] Germany ............................ 44 40 200

[51] Int. Cl.[7] ............................. C12N 15/29; C12N 5/04; C12N 15/82; A01H 5/00; A01H 5/10
[52] U.S. Cl. ....................... 800/303; 800/278; 800/282; 800/287; 536/23.6; 536/24.1; 435/252.3; 435/252.33; 435/320.1; 435/419; 435/421; 435/430.1; 435/468
[58] Field of Search ................... 536/23.6, 24.1; 435/252.3, 252.33, 320.1, 419, 421, 468, 430.1; 800/278, 282, 287, 298, 303

[56] References Cited

U.S. PATENT DOCUMENTS 5,391,724 2/1995 Kindl et al. ............................ 536/23.2
5,500,367 3/1996 Hain et al. ............................ 435/252.3
5,728,570 3/1998 Matern et al. ........................ 435/252.3

FOREIGN PATENT DOCUMENTS

| 335451 | 10/1989 | European Pat. Off. |
| 464461 | 1/1992 | European Pat. Off. |
| 513884 | 11/1992 | European Pat. Off. |
| 516958 | 12/1992 | European Pat. Off. |
| 533010 | 3/1993 | European Pat. Off. |
| 93 18142 | 9/1993 | WIPO |
| 94 18335 | 8/1994 | WIPO |
| WO 94/18335 | 8/1994 | WIPO |

OTHER PUBLICATIONS

Hain et al. Nature 361: 153–156, 1993.
Schöder et al. Eur. J. Biochem. 172(1):161–169, 1988.
Turgut et al. Plant Mol. Biol. 24(1): 97–104, 1994.
Napoli et al. Plant Cell 2:279–289, 1989.
Nature, vol. 361, Jan. 14, 1993, pp. 153–156, Hain, et al., "Disease resistance results . . . plant".
Arch. Biochem. Biophys., vol. 288, 1991, pp. 552–557, XP 000563915, Melchior, F., et al. "Coordinated and elicitor-dependent . . . Optima".
FEBS Letters, vol. 268, No. 1, Jul. 1990, pp. 17–20, Melchior, F., et al., "Grapevine stillbene . . . enzyme".
The Plant Journal (1997) 11(3), pp. 489–498, Fischer et al.

*Primary Examiner*—David T. Fox
*Attorney, Agent, or Firm*—Norris, McLaughlin & Marcus, P.A.

[57] ABSTRACT

The present invention relates to a novel DNA sequence and its use for transforming vectors, host organisms and plants and for producing novel plants which are male-sterile and which exhibit an altered flower color.

34 Claims, 1 Drawing Sheet

DNA SEQUENCES ENCODING STILBENE SYNTHASES AND THEIR USE

This application is a 371 of PCT/EP95/04256 filed Oct. 30, 1995.

BACKGROUND OF THE INVENTION

1. Field of the Invention

The present invention relates to a novel DNA sequence and its use for transforming vectors, host organisms and plants and for producing novel plants which are male-sterile and which exhibit an altered flower colour.

2. Description of Related Art

Male-sterile plants play an important role in plant breeding, in particular in hybrid breeding. A variety of methods for producing male-sterile plants have already been disclosed, which methods involve, for example, eliciting cell damage specifically, for example in the anthers, interfering in mitochondrial functions, using antisense DNA to create opportunities for chemicals to exert a sterilizing effect or inhibiting chalcone synthesis (cf. WO 90/08830, WO 90/08831, WO 89/10396, EP-A-0 329 308 and EP-A-0 335 451). However, the methods which have hitherto been available for producing male-sterile plants do not, in many cases, lead to completely satisfactory results. In addition to this, plants are frequently obtained which exhibit a considerably increased susceptibility towards fungal pathogens, making it substantially more difficult to handle them in practice. There is, therefore, a great need for other methods of producing male-sterile plants which do not suffer from these disadvantages.

The production of plants which exhibit an altered flower colour is of particular interest for ornamental plant breeding, so that there is considerable interest in new methods in this field as well.

SUMMARY OF THE INVENTION

The novel DNA sequence, which is termed DNA sequence I below, has now been found, which sequence consists of the following components, which are sequentially ordered in the 5'-3' direction:

a) a promoter, which is heterologous in relation to component b), which is strongly active in plants and/or which is anther-specific or tapetum-specific, and which is, where appropriate, located downstream of an amplifying element (enhancer);

b) a DNA sequence encoding stilbene synthase; and c) a 3' polyadenylation sequence;

with the term DNA sequence I also encompassing the derived DNA sequences which still exhibit the features which are essential for implementing the invention.

It has furthermore been found that plants which harbour DNA sequence I in their genome are, surprisingly, male-sterile and, in addition to this, exhibit a flower colour which is altered as compared with the corresponding plants which do not contain the DNA sequence I.

These novel plants additionally possess an increased resistance towards microbial plant pathogens, in particular towards phytopathogenic fungi. In many cases, the altered flower colour makes it easier to identify the male-sterile plants readily in a mixed population, something which can be of considerable practical relevance.

The present invention consequently also relates to novel plants (including parts of these plants and their replicative material, such as protoplasts, plant cells, calli, seeds, tubers or cuttings, etc.) which harbour the DNA sequence I in their genome and which are male-sterile and/or exhibit a flower colour which is altered as compared with the corresponding plants which do not harbour the DNA sequence I.

DETAILED DESCRIPTION OF THE INVENTION

Figure 1:
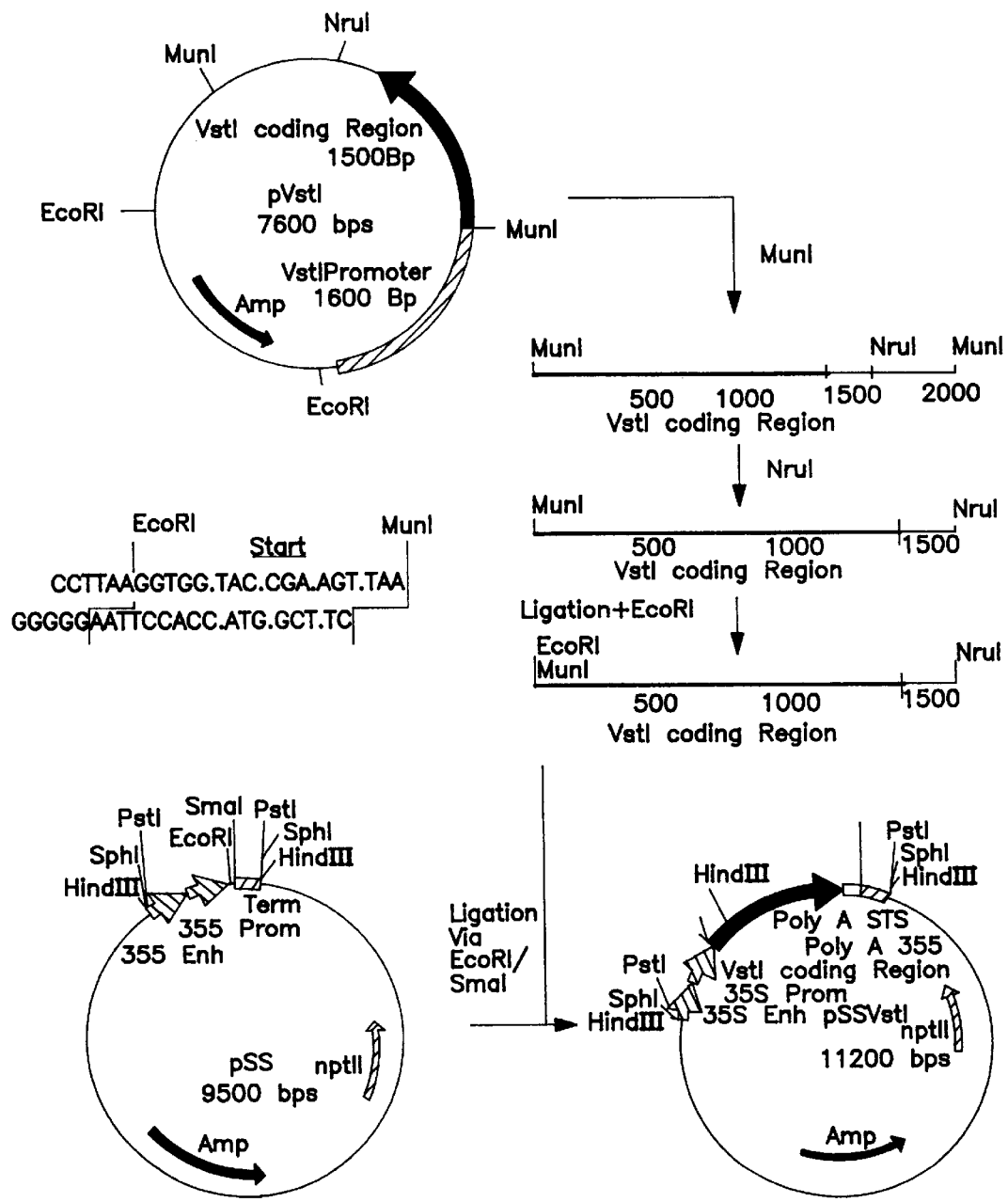
FIG. 1 shows the construction of plasmid pSSVst1.

Promoters which are strongly active in plants and which can be used, in accordance with the invention, as component a) of the DNA sequence I have been disclosed. The promoter of the gene of the small subunit of ribulose-1,5-bisphosphate carboxylase (rbcS) may be mentioned as an example (cf., e.g., EMBO Journal, Vol. 5, No. 9, 2063–2071 (1986)). Furthermore, plant virus promoters which are strongly active in plants may also be employed. Such promoters have been disclosed, and the CaMV 35S promoter (cf., e.g., Science 250: 959–960 (1990)) may be mentioned by way of example.

Anther-specific and/or tapetum-specific promoters may also be used as component a) of the DNA sequence I. Such promoters, which display their activity particularly strongly in the anthers or in the anther site termed the tapetum, have been disclosed. The TA29 promoter may be mentioned as an example (cf., e.g., Nature 347, 737–741 (1990)). The known anther-specific promoters, which have been isolated from tobacco, of the TA26 and TA13 genes are also suitable for use in accordance with the invention.

According to the invention, the CaMV 35S promoter is preferably used as component a) of the DNA sequence I.

It can be advantageous to place a suitable amplifying element (enhancer) upstream of the promoter in order to amplify the desired effect of the promoter. Such enhancer/promoter constructs have been disclosed. The known CaMV 35S enhancer, for example, may particularly advantageously be employed as the enhancer.

According to the invention, the CaMV 35S promoter is particularly preferably used as component a) of the DNA sequence I. Very particularly preferably, a construct is employed which consists of the CaMV 35S enhancer and, which follows it in the CaMV 35S promoter the 5'-3' direction.

The promoter which is to be used in accordance with the invention is heterologous with regard to component b), i.e. is different from promoters which are found in natural stilbene synthase genes.

The isolation of suitable promoters and enhancers has been disclosed or can be effected using known processes and methods with which the skilled person is familiar.

Any DNA which encodes the enzyme stilbene synthase may be used as component b) in the DNA sequence I. Stilbene synthase is understood to mean any enzyme which is able (in a suitable environment, in particular in plant cells) to produce stilbenes. The term stilbenes describes a group of chemical substances which are found in plants and which contain the stilbene skeleton (trans-1,2-diphenylethylene) as their common basic structure. This basic skeleton can also be augmented by the addition of further groups. Two important and preferred stilbenes are 3,5-dihydroxy-stilbene (pinosylvine) and 3,4',5-trihydroxy-stilbene (resveratrol).

DNA sequences which encode stilbene synthase have been disclosed, for example, in European Patent Applications EP-A-0 309 862, EP-A-0 464 461 and EP-A-0 533

010. These patent applications describe the isolation of stilbene synthase genes and their use for producing transgenic plants which exhibit an increased resistance to pathogens. The stilbene synthase-encoding DNA sequences which are described in these patent applications are preferably employed in accordance with the invention, with particular preference being given to the sequences which encode resveratrol synthase. In addition, preference is given to employing the stilbene synthase-encoding DNA sequences from groundnut plants (*Arachis hypogaea*) and grape vine (*Vitis vinifera*) which are described in the said European patent applications. The DNA sequences which encode stilbene synthase may be present in the form in which they are contained in the corresponding natural plant genes ("genomic form") including the noncoding regions (such as introns) which may be present, or in a form which corresponds to the cDNA (copy DNA) which can be obtained from mRNA using reverse transcriptase/polymerase and no longer contains any introns. The sequences may also be present in a form which is partially or completely synthetic or be assembled from moieties of differing origin.

The stilbene synthase-encoding DNA sequences which are contained in the plasmid pGS828.1 (EP-A-0 309 862), the plasmid pin5-49 (EP-A-0 533 010) and, very particularly preferably, the plasmids pVst1, pVst2 and pVst12t3 (EP-A-0 464 461) are particularly preferably employed in accordance with the invention, as are the additional stilbene synthase-encoding DNA sequences which can be isolated from plants with the aid of these DNA sequences (which are used as probes). Particular emphasis is given to the stilbene synthase-encoding sequence which is contained in plasmid pVst1 (EP-A-0 464 461).

The isolation of the DNA sequences which can be used as component b) of the DNA sequence I has been disclosed and/or can be effected using the processes and methods which are known and which are familiar to the skilled person. The region encoding stilbene synthase may, for example, be isolated from plasmids pVst1, pVst2 pVst12t3 or pGS828.1 using the polymerase chain reaction technique (PCR technique).

The amplification can be effected by PCR using, e.g., the following programmes:

| | |
|---|---|
| 1x | 95° C. 180 sec |
| | 72° C. hold (addition of polymerase) |
| 25x | 95° C. 45 sec |
| | 55° C. 45 sec |
| | 72° C. 90 sec |
| 1x | 95° C. 45 sec |
| | 55° C. 45 sec |
| | 72° C. 300 sec |

The Vst1 and Vst2 stilbene synthase genes from Vitis vinifera (var. optima) and the stilbene synthase gene from *Arachis hypogaea* (A. hyp.) can be amplified using the following primers:

Primer 1 Vst1: see SEQ ID NO: 1

Primer 1 Vst2: see SEQ ID NO: 2

Primer 1 A. hyp.: see SEQ ID NO: 3

Primer 2 Vst1: see SEQ ID NO: 4

Primer 2 Vst2: see SEQ ID NO: 5

Primer 2 A. hyp.: see SEQ ID NO: 6

All the coding regions, which have thus been amplified, of the individual genes can be ligated into the appropriate restriction cleavage sites of customary vectors.

In addition, the coding and the terminating sequence can also be isolated together from pSSVst1 (cf. below) using the enzymes EcoRI and PstI and also EcoRI and SphI.

The 3' polyadenylation sequence which is contained in the DNA sequence I as component c) may be varied to a large extent, so that all the appropriate sequences can be used which do not have a detrimental effect on the expression of the stilbene synthase in plants. It can also be expedient to employ several (e.g. two) polyadenylation sequences, where appropriate of differing origin, which are inserted one after the other, in particular when this ensues as a result of the techniques which are used on a particular occasion (cf. moiety c) in SEQ ID NO: 7). For the sake of simplicity, use is preferably made of the 3' polyadenylation sequence which is contained in natural stilbene synthase genes, with this sequence expediently being isolated from the stilbene synthase genes together with the stilbene synthase-encoding sequence. Consequently, stilbene synthase genes from which only the natural promoter has been removed may also be employed, according to the invention, as components b) and c). In this case, it is only necessary to add on component a) of the DNA sequence I, that is the heterologous promoter and, where appropriate, the enhancer, upstream.

Suitable 3' polyadenylation sequences can be isolated using processes and methods which are generally customary and which are familiar to the skilled person.

The DNA sequences according to SEQ ID NO: 7, either individually or in the existing combination, are very particularly preferably used as components a) to c) of DNA sequence I. In SEQ ID NO: 7, nucleotides 1 to 720 constitute the double 35S CaMV RNA promoter, which consists of the CaMV 35S enhancer and the CaMV 35S promoter (component a)). Nucleotides 721 to 730 are a synthetic linker sequence. Nucleotides 731 to 2265 of SEQ ID NO: 7 represent the moiety encoding stilbene synthase (component b)) and nucleotides 2266 to 2485 represent the polyA moiety (component c)) of the stilbene synthase gene. The nucleotides from 2486 to 2728 represent the moiety of component c) which is derived from CaMV 359 RNA, with polylinker sequences being present at the end.

The term DNA sequence I also includes all the derived DNA sequences which still exhibit the features which are essential for implementing the invention, which sequences consequently elicit male sterility, and may elicit a change in flower colour, in plants. In such derived sequences, individual DNA's, codons and/or constituent sequences may be lacking (for example due to the use of restriction enzymes) and/or replaced by other DNA's, codons and/or constituent sequences. These modifications may be present due to the degeneracy of the genetic code or arise during manipulation of the DNA sequences. The novel DNA sequences and/or their components a) to c) may also contain DNA's and/or DNA sequences which make them easier to handle, for example so-called linkers or those of these linkers which remain after manipulating (for example after cutting with restriction enzymes). Components a) to c) of the DNA sequence I can be of natural origin or be present in a form which is partially or completely synthesized.

Components a) to c) can be joined to form the DNA sequence I, which can also be regarded as a "chimeric gene", using the processes and methods which are generally customary and which are familiar to the skilled person.

In a particular embodiment of the invention, the DNA sequence I consists of (a) the so-called CaMV 35S double promoter, which is made up of the CaMV 35S promoter and the appurtenant CaMV 35S enhancer, and (b) the sequence encoding stilbene synthase (resveratrol synthase), together with the following 3' polyadenylation sequence, as is present in plasmid pVst1 (cf. EP-A-0 464 461).

This DNA sequence is contained in the novel plasmid pSSVst1, whose construction is shown in FIG. 1. The coding region of the stilbene synthase gene Vst1 can, accordingly, be isolated, as a 2.1 kB MunI fragment, from plasmid pVst1, which contains the complete stilbene synthase gene (Vst1 gene) as a 4.9 kB EcoRI fragment. However, this MunI fragment lacks the first 4 codons at the 5' end of the coding region. Expediently, the purified MunI fragment is subsequently digested with restriction enzyme NruI and the resulting 1.7 kB NruI/MunI fragment is fused to an oligonucleotide linker which encodes the first four amino acids. Since the protruding ends of the EcoRI and MunI restriction cleavage sites are identical and it is necessary to prevent a MunV/EcoRI fusion, the oligonucleotide linker is designed such that the EcoRI cleavage site is only formed by a subsequent restriction digestion. The resulting NruI/EcoRI fragment is ligated between the SmaI and EcoRI cleavage sites of the shuttle vector pSS such that the complete coding region of the Vst1 stilbene synthase gene is under the control of the double 35S promoter. However, corresponding constructs can be prepared, using the customary methods, by the skilled person on the basis of his specialist knowledge and the information contained in the present text, and then put to use.

The *Escherichia coli* strain RH pSSVst1 harbours plasmid pSSVst1. This *E. coli* strain, RH pSSVst1, was deposited in the Deutsche Sammlung von Mikro-organismen (DSM) [German collection of microorganisms], Mascheroder Weg 1B, D-38124 Braunschweig, Federal Republic of Germany, in conformity with the requirements of the Budapest treaty on the international deposition of micro-organisms for the purposes of patent processes, on Oct. 18, 1994, and was given the deposition number DSM 9501.

Plasmid pSSVst1, and *E. coli* strain RH pSSVst1, and its mutants which still exhibit the features of the deposited strain which are essential for implementing the invention, are likewise part of the present invention.

*E. coli* strain RH pSSVst1 can be replicated using the methods which are generally customary. Plasmid pSSVst1 can likewise be isolated from this *E. coli* strain using the methods which are generally customary. It is also an easy matter for the skilled person to isolate the DNA sequence I which is contained in plasmid pSSVst1. Thus, the DNA sequence I which is contained in plasmid pSSVst1 can, for example, be isolated from this plasmid, in the form of an approximately 2700 bp (base pair)-sized DNA fragment, using the restriction enzymes SphI and PstI.

It is possible, using the methods which are customary and which are familiar to the skilled person, to incorporate the DNA sequence I once or more than once (e.g. tandem arrangement), preferably once, as "foreign" DNA, into any prokaryotic (preferably bacterial) or eukaryotic (preferably plant) DNA. The recombinant DNA which has thus been "modified", and which can be used, for example, for transforming plants or plant cells, and which, after the transformation, is contained in plants or plant cells, is a constituent part of the present invention.

The DNA sequence I, and the recombinant DNA, can be contained, as "foreign" DNA, in vectors (in particular plasmids, cosmids or phages), in transformed microorganisms (preferably bacteria, in particular Gram-negative bacteria, such as *E. coli*) and also in transformed plant cells and plants, or in their DNA. Such vectors, transformed microorganisms (which may also harbour these vectors) and also the transformed plant cells and plants, and their DNA, represent constituent parts of the present invention. As already intimated, the DNA sequence I is, according to the invention, incorporated once or more than once (at the same or different sites in the genome) into the natural plant genome.

The present invention consequently also relates to a process for preparing transgenic plant cells (including protoplasts) and plants (including plant parts and seeds), where these plants are male-sterile and may exhibit an altered flower colour, which process is characterized in that (a) the DNA sequence I and/or novel recombinant DNA is/are inserted, once or more than once, into the genome of plant cells (including protoplasts) and, where appropriate, (b) complete, transformed plants are regenerated from the transformed plant cells (including protoplasts) and, where appropriate, replicated, and, where appropriate, (c) the desired plant parts (including seeds) are isolated from the resulting transgenic plants of the parental generation or other generations which are obtained therefrom.

Process steps (a), (b) and (c) can be carried out, in a customary manner, using known processes and methods.

Transgenic plant cells (including protoplasts) and plants (including plant parts and seeds) which harbour, once or more than once, the DNA sequence I, as "foreign" DNA, and the descendants thereof, and also those transformed plant cells and plants which can be obtained using the above processes, and the descendants thereof, likewise belong to the present invention.

The following are also parts of the present invention:

(a) the use of the DNA sequence I and/or the novel recombinant DNA and/or the novel recombinant vectors and/or the novel transformed micro-organisms for transforming plant cells (including protoplasts) and plants (including plant parts and seeds), (b) the use of the novel transgenic plant cells (including protoplasts) and plants (including plant parts and seeds) for producing replicative material and also for producing new plants and their replicative material, (c) the use of the novel DNA sequence I and/or the novel recombinant DNA for producing male sterility and, where appropriate, an altered flower colour in plants, (d) the use of the DNA sequence I, which is contained in plasmid pSSVst1, for detecting the presence of the DNA sequence I in plants and also (generally) in the production of transgenic plant cells (including protoplasts) and plants (including plant parts and seeds), and also (e) the use of the stilbene synthase-encoding DNA sequence for producing transgenic plants which are male-sterile and/or exhibit a flower colour which is altered as compared with corresponding plants which do not harbour this DNA in their genome.

A number of different methods are available for incorporating the DNA sequence I, as "foreign" DNA, into the genetic material of plants or plant cells. The gene transfer can be effected using the generally customary, known methods, with it being possible for the skilled person to ascertain without difficulty the suitable method in each case.

The Ti plasmid of *Agrobacterium tumefaciens* is available as a particularly favourable and widely applicable vector for transferring foreign DNA into the genomes of dicotyledonous and monocotyledonous plants. For this, the DNA sequence I is inserted, in an appropriate manner, into the T-DNA of suitable Ti plasmids (e.g. Zambryski et al., 1983) and transferred by infecting the plant, infecting plant parts or plant tissues, such as leaf discs, stems, hypocotyles, cotyledons or meristems, and tissues derived therefrom, such as secondary embryos and calli, or by coculturing protoplasts with *Agrobacterium tumefaciens.*

An alternative is to incubate the DNA sequence I, or recombinant DNA, with plant protoplasts (e.g. Hain et al., 1985; Krens et al., 1982; Paszkowski et al., 1984) in the presence of polycations or calcium salts and polyethylene glycol.

The DNA uptake can also be additionally assisted by means of an electrical field (electroporation) (e.g. Fromm et. al., 1986).

The DNA can also, in a known manner, be introduced by way of plant pollen, for example by "bombarding" pollen or plant tissue with physically accelerated particles which are carrying the DNA (cf. EP-A 0 270 356).

The plants are regenerated in a known manner using suitable nutrient media (e.g. Nagy and Maliga 1976).

In a preferred embodiment of the novel process (according to the method from EP-A 116 718), the DNA sequence I, as contained in plasmid pSSVst1, is cloned into a suitable intermediate *E. coli* vector, for example pGV700 or pGV710 (cf. EP-A-116 718), or preferably derivatives thereof which additionally contain a reporter gene such as npt11 (Herrera-Estrella et al. 1983) or hpt (Van den Elzen et al. 1986).

The plasmid which has been constructed in this way is transferred, using customary methods (e.g. Van Haute et al. 1983), into *Agrobacterium tumefaciens* which harbours pGV 3850, for example, or derivatives thereof (Zambryski et al. 1983). Alternatively, the DNA sequence I can be cloned into a shuttle vector, for example PCV001 or PCV002 (e.g. Koncz and Schell 1986) and transferred, as described above, into a suitable Agrobacterium strain (Koncz and Schell 1986). The resulting Agrobacterium strain, which harbours the DNA sequence I in a form which is transferrable to plants, is then used for the plant transformation. Plasmid pSSVst1 can also be introduced directly into a suitable *A. tumefaciens* strain (cf., e.g., Koncz and Schell (1986)).

In another preferred embodiment, plasmid pSSVst1, which contains a kanamycin-resistance reporter gene for plant cells (e.g. Herrera-Estrella et al. 1983), is transferred, by direct gene transfer, in a customary manner, into plant protoplasts (e.g. Hain et al., 1985). While plasmid pSSVst1 can be in circular form for this purpose, it is preferably in linear form. When pSSVst1 containing the reporter gene is used, kanamycin-resistant protoplasts are then examined for expression of stilbene synthases.

Transformed (transgenic) plants or plant cells are produced in accordance with known methods, for example by means of transforming leaf discs (e.g. Horsch et al., 1985), by means of coculturing regenerating plant protoplasts or cell cultures with *Agrobacterium tumefaciens* (e.g. Marton et al., 1979, Hain et al., 1985) or by means of direct transfection with DNA. Resulting transformed plants are detected either by selecting for expression of the reporter gene, for example by the phosphorylation of kanamycin sulphate in vitro (Reiss et al., 1984; Schreier et al. 1985) or by screening for expression of nopaline synthase (in accordance with Aerts et al. 1983) or stilbene synthase by means of Northern blot analysis and Western blot analysis. The stilbene synthase, and the stilbenes, can also be detected in transformed plants, in a known manner, with the aid of specific anti-bodies. Stilbene synthase can also be detected by means of an enzyme activity test (Rolfs et al., Plant Cell Reports 1, 83–85, 1981).

Cultivation of the transformed plant cells and regeneration into complete plants are carried out in accordance with the generally customary methods, using the nutrient media which are suitable in each case.

Both the transformed plant cells and the transformed plants which harbour the novel DNA sequence I, and which are constituent parts of the present invention, exhibit a substantially greater resistance to pathogens, in particular phytopathogenic fungi.

In connection with the present invention, the term "plants" denotes complete plants, plant parts, such as leaves, stems or roots, and replicative material, such as seeds, tubers, cuttings, etc. "Plant cells" encompasses protoplasts, cell lines, plant calli, etc.

As has already been explained, plants which harbour the novel DNA sequence I in their genome exhibit male sterility and may also exhibit a flower colour which is altered as compared with the corresponding plants which do not harbour the DNA sequence I.

In the case of ornamental plants and flowers for cutting, for example roses, carnations, freesias, gerbera, etc., the flower colour is of considerable commercial importance. Influencing flower colours in a specific manner, and achieving stable flower colours, is frequently a difficult and elaborate matter. The present invention makes it possible, in a relatively simple manner, to alter the flower colour of all plants which have coloured flowers and which possess flower pigments, in particular anthocyanins. As a rule, the flowers become lighter, and frequently completely white, as a result of incorporation of the DNA sequence I. In general, a change cannot be identified, or can only be identified with difficulty in the case of plants which do not have coloured flowers.

The male sterility of plants plays a very important role in plant breeding with regard to the production of hybrid lines and hybrid seeds. Unfortunately, many hybrid lines are very susceptible to phytopathogenic fungi, thereby greatly restricting their usability. Male-sterile plants can be produced relatively simply with the aid of the present invention. These plants additionally exhibit an increased resistance towards microbial plant pathogens such as phytopathogenic fungi, bacteria and/or viruses, in particular towards phytopathogenic fungi, and are consequently superior to male-sterile plants which are obtained using other methods.

Practically all plants are included in the plants which can be rendered male-sterile by incorporation (transformation) of the novel DNA sequence I. Naturally, there is a particular need in this regard in the case of cultivated plants such as plants which supply foodstuffs and raw materials, for example cereal plants (in particular wheat, rye, barley, oats, millet, rice and maize), potatoes, leguminosae (such as pulse crops and, in particular, alfalfa and soya beans), vegetables (in particular cabbage varieties and tomatoes), fruit (in particular apples, pears, cherries, grapes, citrus fruits, pineapples and bananas), oil palms, tea, cocoa and coffee bushes, tobacco, sisal and cotton, and also in he case of medicinal plants, such as rauwolfia and digitalis. Rice, wheat, barley, rye, maize, sugar beet, rape and soya may be mentioned as being particularly preferred.

The following exemplary embodiments are intended to clarify the present invention:

I) Transformation of plants

1. Construction and description of vector pSSVst1

The construction of plasmid pSSVst1 has already been explained in detail above and is depicted in FIG. 1 in such a way that it can be readily comprehended by the skilled person.

Plasmid pSSVst1 is a derivative of pSS. pSS is a derivative of PCV001 (Koncz and Schell, 1986), which contains an expression cassette which is based on plasmid pRT101 (Töpfer et al., 1987) and in which the CaMV 35S RNA enhancer has been duplicated by cloning the Ddel/EcoRV fragment into the Hinc11 cleavage site. pSSVst1 contains the coding sequence and the polyA sequence of pVst1 stilbene synthase (cf. FIG. 1). pSSVst1 contains a plant kanamycin resistance and a bacterial ampicillin resistance. In addition, pSSVst1 contains border sequences from the Agrobacterium tumefaciens Ti-plasmid and a replication start for A. tumefaciens and E. coli (Koncz and Schell, 1986). Plasmid pSSVst1 can be mobilized directly into a suitable Agrobacterium tumefaciens strain (e.g. Koncz and Schell 1986) using the strain E. coli RH pSSVst1.

2. Transformation of tobacco a) Culturing tobacco shoots and isolation of tobacco protoplasts:

Nicotiana tabacum (Petit Havana SR1) is replicated as a sterile shoot culture on hormone-free LS medium (Linsmaier and Skoog 1965). At intervals of approx. 6–8 weeks, shoot segments are transferred to fresh LS medium. The shoot cultures are kept in a culture room at 24–26° C. while being exposed to 12 h of light (1000–3000 lux).

In order to isolate leaf protoplasts, approx. 2 g of leaves (approx. 3–5 cm in length) are cut into small pieces (0.5 cm×1 cm) using a fresh razor blade. The leaf material is incubated, at room temperature for 14–16 h, in 20 ml of enzyme solution, consisting of K3 medium (Nagy and Maliga 1976), 0.4 m sucrose, pH 5.6, 2% RIO cellulase (Serva), 0.5% R10 Macerozyme (Serva). After that, the protoplasts are separated from cell residues by filtration through 0.30 mm and 0.1 mm steel sieves. The filtrate is centrifuged at 100×g for 10 minutes. During this centrifugation, the intact protoplasts float and collect in a band at the upper margin of the enzyme solution. The pellet, consisting of cell residues, and the enzyme solution are sucked off using a glass capillary. The prepurified protoplasts are made up to 10 ml with fresh K3 medium (0.4 M sucrose as osmotic agent) and floated once again. The wash medium is sucked off and the protoplasts are diluted to 1–2× $10^5$/ml for culture and subsequent infection with agrobacteria (coculture). The protoplast concentration is determined in a counting chamber.

b) Transformation of regenerating tobacco protoplasts by coculture with Agrobacterium tumefaciens:

In that which follows, the method of Marton et al. 1979 is used with slight modifications. The protoplasts are isolated as described and incubated, at 26° C. and at a density of 1–2×$10^5$/ml, in K3 medium (0.4 m sucrose, 0.1 mg/l NAA, 0.2 mg of kinetin) for 2 days in the dark and for from 1 to 2 days under weak light (500 lux). As soon as the first divisions of the protoplasts appear, 30 µl of a suspension of agrobacteria, which harbour the sequence I in their T-DNA or harbour plasmid pSSVst1, in minimal A (Am) medium (density, approx. $10^9$ agrobacteria/ml), are added to 3 ml of regenerating protoplasts. The duration of the coculture, at 20° C. and in the dark, is 3–4 days. After that, the tobacco cells are loaded into 12 ml centrifuge tubes, diluted to 10 ml with sea water (600 mOsm/kg) and pelleted at 60×g for 10 minutes. This washing procedure is repeated a further 1–2× in order to remove the majority of the agrobacteria. The cell suspension is cultured, at a density of 5×$10^4$/ml, in K3 medium (0.3 m sucrose) containing I mg of NAA (naphthyl-1-acetic acid) per 1, 0.2 mg of kinetin per 1 and 500 mg of the cephalosporin antibiotic cefotaxime per 1. Each week, the cell suspension is diluted with fresh K3 medium and the osmotic volume of the medium is gradually reduced by 0.05 m sucrose (approx. 60 mOsm/kg) per week. Selection with kanamycin (100 mg/l kanamycin sulphate (Sigma), 660 mg/g active Km) is started in agarose bead-type culture (Shillito et al. 1983) 2–3 weeks after the coculture. 3–4 weeks after beginning the selection, it is possible to distinguish kanamycin-resistant colonies from the background of retarded colonies.

c) Direct transformation of tobacco protoplasts with DNA. Calcium nitrate/PEG transformation Approx. $10^6$ protoplasts in 180 µl of K3 medium are carefully mixed, in a petri dish, with 20 µl of aqueous DNA solution which contains 0.5 µg of plasmid pSSVst1, or the isolated DNA sequence I from pSSVst1, per µl, as the DNA fragment, and 0.5 µl of pLGVneo2103 per µl (Hain et al. 1985). 200 µl of fusion solution (0.1 m calcium nitrate, 0.45 M mannitol, 25% polyethylene glycol (PEG 6000), pH 9) are then added carefully. After 15 minutes, 5 ml of wash solution (0.275 M calcium nitrate, pH 6) are added and, after a further 5 minutes, the protoplasts are transferred into a centrifuge tube and pelleted at 60×g. The pellet is taken up in a small quantity of K3 medium and cultured as described in the next section. Alternatively, the protoplasts can be transformed as described by Hain et al. 1985.

The transformation with the DNA sequence I from pSSVst1 can also be carried out without adding the 0.5 µg of pLGVneo2103 per µl. Since no reporter gene is employed in this case, dot blot hybridization is used to examine the resulting calli for the presence of the DNA sequence I gene unit. The coding sequence from pSSVst1 can be used as the hybridization probe. Naturally, other detection methods, such as tests with antibodies or an enzyme test for stilbene synthase, can also be employed.

d) Culturing the protoplasts which have been incubated with DNA and selecting kanamycin-resistant calli:

A modified bead-type culture technique (Shillito et al. 1983) is used for the culture and selection of kanamycin-resistant colonies described below. One week after treating the protoplasts with DNA (cf. c), 3 ml of the cell suspension are mixed, in 5 cm petri dishes, with 3 ml of K3 medium (0.3 M sucrose+hormones; 1.2% (Seaplaque) LMT agarose (low-melting agarose, Marine colloids). For this purpose, agarose is autoclaved in the dry state, and, after K3 medium has been added, is boiled briefly in a microwave oven. After the agarose has solidified, the agarose beads containing the embedded tobacco microcalli are transferred, for further culture and selection, into 10 cm petri dishes and in each case 10 ml of K3 medium (0.3 M sucrose, 1 mg/l NAA, 0.2 mg/l kinetin) and 100 mg/l kanamycin sulphate (Sigma) are added. The liquid medium is changed each week. In association with this, the osmotic value of the medium is lowered stepwise.

The sucrose concentration in the replacement medium (K3+Km) is reduced by 0.05 m (approx. 60 mOsm) each week.

Scheme for selecting kanamycin-resistant tobacco colonies following DNA transformation:

| 0.4 M | 0.3 M | 0.25 M | 0.20 M | 0.15 M | 0.10 M | Sucrose in the liquid medium |
|-------|-------|--------|--------|--------|--------|------------------------------|
| U     | E S   |        |        |        | K      |                              |
|       | 1     | 2      | 3      | 4      | 5      | 6 weeks after DNA uptake     |

(K3 medium, 1 mg of NAA, 0.2 mg of kinetin)
U=DNA uptake
E=embedding in agarose
S=selection with kanamycin (100 mg of kanamycin sulphate/l)
K=kanamycin-resistant colonies can be clearly distinguished from the background e) Regeneration of kanamycin-resistant plants:

As soon as the kanamycin-resistant colonies have reached a diameter of approx. 0.5 cm, half of them are placed on regeneration medium (LS medium, 2% sucrose, 0.5 mg/l benzylaminopurine BAP) and kept at 24° C. in a culture room while being exposed to 12 h of light (3000–5000 lux). The other half is propagated as a callus culture on LS medium containing 1 mg/l NAA, 0.2 mg/l kinetin, 0.1 mg/l BAP and 100 mg/l kanamycin sulphate. When the regenerated shoots are approx. 1 cm in size, they are cut off and placed, for rooting, on ½ LS medium (1% sucrose, 0.8% agar) without growth regulators. The shoots are rooted on ½ MS medium containing 100 mg/l kanamycin sulphate and subsequently transplanted into soil.

f) Transformation of leaf discs with *Agrobacterium tumefaciens*

For the transformation of leaf discs (Horsch et al. 1985), leaves of approx. 2–3 cm in length from sterile shoot cultures are punched into discs of 1 cm in diameter and incubated, for approx. 5 minutes, with a suspension (approx. $10^9$/ml) (cf. b) of appropriate agrobacteria, which harbour plasmid pSSVst1 or the DNA sequence I from this plasmid in their T-DNA, in Am medium (see below). The infected leaf pieces are kept at approx. 24° C. for 3–4 days on MS medium (see below) without hormones. During this time, Agrobacterium overgrows the leaf pieces. The leaf pieces are then washed in MS medium (0.5 mg/ml BAP, 0.1 mg/ml NAA) and placed on the same medium (0.8% agar) containing 500 Hg/ml cefotaxime and 100 Hg/ml kanamycin sulphate (Sigma). The medium should be renewed after two weeks. Transformed shoots are visible after a further 2–3 weeks.

Biochemical method for detecting transformation

Neomycin phosphotransferase (NPT II) enzyme test:

NPT II activity in plant tissue is detected by the in-situ phosphorylation of kanamycin, as described in Reiβ et al. (1984) and modified by Schreier et al. (1985), as follows. 50 mg of plant tissue are homogenized, on ice and in the presence of added glass powder, in 50 µl of extraction buffer (10% glycerol, 5% 2-mercaptoethanol, 0.1% SDS, 0.025% bromophenol blue, 62.5 mM Tris, pH 6.8) and centrifuged, at 4° C. for 10 minutes, in an Eppendorf centrifuge. 50 µl of the supernatant are loaded onto a native polyacrylamide gel (145×110×1.2 mm; resolving gel: 10% acrylamide, 0.33% bisacrylamide, 0.375 M tris, pH 8.8, stacking gel: 5% acrylamide, 0.165% bisacrylamide, 0.125 M tris, pH 6.8) and electrophoresed overnight at 4° C. and 60 V. As soon as the bromophenol blue marker has run out of the gel, the latter is washed twice with distilled water for 10 min and once with reaction buffer (67 mM Tris-maleate, pH 7.1, 42 mM $MgCl_2$, 400 mM ammonium chloride) for 30 min. The gel is laid on a glass plate of the same size and overlaid with 40 ml of 1% agarose in reaction buffer which contains the substrates kanamycin sulphate (20 Hg/ml) and 20–200 Ci of $^{32}$P ATP (Amersham). The sandwich gel is incubated at room temperature for 30 min and a sheet of phosphocellulose P81 paper (Whatman) is then laid on the agarose. Four layers of 3 mm filter paper (Whatman) and some paper towels are piled on top. The transfer of in-situ phosphorylated, radioactive kanamycin phosphate to the P81 paper is stopped after 3–4 h. The P81 paper is incubated, at 60° C. for 30 min., in a solution of proteinase K and 1% sodium dodecyl sulphate (SDS) and then washed, at 80° C., 3–4 times in 250 ml of 10 mM phosphate buffer, pH 7.5, dried and autoradiographed (Kodak XAR5 film) at −70° C. for 1–12 h.

The presence of the DNA sequence encoding stilbene synthase in the plant cells and plants (tobacco) which were obtained in accordance with the above examples was confirmed by Southern blot analysis. Expression of the sequence encoding stilbene synthase was demonstrated by Northern blot analysis, while stilbene synthase and resveratrol were demonstrated with the aid of specific antibodies. Transformed plants and nontransformed plants (for comparison) were cultivated in a greenhouse through to flowering. The transformed plants exhibited a flower colour which was altered (as compared with the nontransformed comparison plants) and were mate-sterile.

The media employed in transforming plants and plant cells are described, inter alia, in EP-A 0 309 862:

All the percentage values in the above examples and in the example below refer to percentages by weight, unless otherwise indicated.

II) Checking the transgenic plants for altered flower colour and for male sterility.

EXAMPLE A

The transgenic tobacco plants which were obtained in accordance with the above examples are preraised in tissue culture and then raised, through to flowering, in a greenhouse at 23° C. and 70–80% relative atmospheric humidity. They are supplied with fertilizer and water as required.

All the plants which were transformed in accordance with Example I) exhibited a white or whitish-pink flower colour which was retained in the F1 generation even after backcrossing with the wild type, whereas the corresponding control plants, which had not been transformed, exhibited a strong red, dark pink or crimson colour.

All the transformed plants were also male-sterile, with this sterility being retained in the F1 generation as well.

The following publications may be cited with regard to the transformation of plants:

Fraley R T, Rogers S G, Horsch R B, Sanders P R, Flick J S, Adams S P, Bittner M L, Brand L A, Fink C L, Fry J S, Fallupi G R, Goldberg S B, Hoffmann N L, Woo S C (1983). Expression of bacterial genes in plant cells. Proc. Natl. Acad. Sci. USA 80:4803–4807.

Fromm M E, Taylor L P, Walbot V (1986) Stable transformation of maize after gene transfer by electroporation. Nature 319: 791–793.

Hain R, Stabel P, Czernilofsky, A P, Steinbiβ, H H, Herrera-Estrella, L Schell, J (1985) Uptake, integration, expression and genetic transmission of a selectable chimeric gene by plant protoplasts. Molec Gen Genet 199: 161–168.

Hain R, Bieseler B, Kindl H, Schroder G, Stöcker R (1990) Expression of a stilbene synthase gene in *Nicotiana tabacum* results in synthesis of the phytoalexin resveratrol. Plant Mol, Biol. 15:325–336.

Hain R, Reif H J, Krause E, Langbartels R, Kindl H, Vornam B, Wiese W, Schnetzer E, Schreier P H, Stöcker R H, Stenzel K (1993) Discase resistance results from foreign phytoalexin expression in a novce plant. Nature 361: 153–156.

Hernalsteens J P, Thia-Tong L, Schell J, Van Montagu M (1984) An Agrobacterium-transformed Cell culture from the monocot *Asparagus officinalis*. EMBO J 3:3039–3041.

Herrera-Estrella L, De Block M, Messens E, Hernalsteens J P, van Montagu M, Schell J (1983) EMBO J. 2: 987–995.

Horsch R B, Fry J E, Hoffmann N L, Eichholtz D, Rogers S G, Fraley R T (1985) A simple and general method for transferring genes into plants. Science 277: 1229–1231.

Krens F H, Molendijk, Wullems G J, Schilperoort R A (1982) In vitro transformation of plant protoplasts with Ti-plasmid DNA. Nature 296: 72–74.

Koncz C, Schell J (1986) The promoter of $T_L$-DNA gene 5 controls the tissue-specific expression of chimeric genes carried by a novel type of Agrobacterium linary vector. Mol. Gen. Genet. (1986) 204: 338–396.

Linsmaier D M, Skoog F (1965) Organic growth factor requirements of tobacco tissue cultures. Physiol Plant 18: 100–127.

Marton L, Wullems G J, Molendijk L, Schilperoort P R (1979) In vitro transformation of cultured cells from *Nicotiana tabacum* by *Agrobacterium tumefaciens*. Nature 277: 1229–131.

Melchior F, Kindl H (1990) Grapevine stilbene synthase cDNA only slightly differing from chalcone synthase cDNA is expressed in *Escherichia coli* into a catalytically active enzyme FEBS 268:17–20.

Nagy J I, Maliga P (1976) Callus induction and plant regeneration from mesophyll protoplasts of *Nicotiana sylvestris*. Z Pflanzenphysiol 78: 453–455.

Otten L A B M, Schilperoort R A (1978) A rapid microscale method for the detection of Lysopin and *Nopalin dehydrogenase* activities. Biochim biophys acta 527: 497–500.

Paszkowski J, Shillito R D, Saul M, Mandak V, Hohn T, Hohn B, Potrykus I (1984) Direct gene transfer to plants. EMBO J 3:2717–2722.

Rolf C H, Fritzemeier K H and Kindl H (1981) Cultured cells of *Arachis hypogaea* susceptible to induction of stilbene synthase (resveratrol forming) Plant Cell. Rep. 1:83–85.

Schröder G, Brown J W S and Schröder J (1988) Molecular analysis of resveratrol synthase: cDNA, genomic clones and relationship with chalconsynthase. Eur. J. Biochem. 172, 161–169.

Shillito R D, Paszkowski J, Potrykus I (1983) Agarose plating and Bead type culture technique enable and stimulate development of protoplast-derived colonies in a number of plant species. P1 Cell Rep 2: 244–247.

Van den Elzen P J M, Townsend J, Lee K Y, Bedbrook J R (1985) A chimaeric resistance gene as a selectable marker in plant cells. Plant Mol. Biol. 5, 299–302.

Velten J, Velten L, Hain R, Schell J (1984) Isolation of a dual plant promoter fragment from the Ti Plasmid of *Agrobacterium tumefaciens*. EMBO J 12: 2723–2730.

Van Haute E, Joos H, Maes M, Warren G, Van Montagu M, Schell J (1983) Intergenic transfer and exchange recombination of restriction fragments clones in pBR 322: a novel strategy for the reversed genetics of Ti plasmids of/*Agrobacterium tumefaciens*. EMBO J 2: 411–418.

Zambryski P, Joos H, Genetello C, van Montagu M, Schell J (1983) Ti-plasmid vector for the introduction of DNA into plant cells without altering their normal regeneration capacity, ENBO J 12: 2143–2150.

Reiss, B, Sprengel, Will H and Schaller H (1984) A new sensitive method for qualitative and quantitative assay of neomycin phosphotransferase in crude cell tracts, GENE 1081: 211–217.

Schreier P H, Seftor E A, Schell J and Bohnert H J (1985) The use of nuclear encoded sequences to direct the light-regulated synthesis and transport of a foreign protein into plant chloroplasts, EMBO J Vol. 4, No. 1: 25–32.

In addition, the following published patent applications may be listed:

| | |
|---|---|
| EP-A 116 718 | EP-A-126 546 |
| EP-A 159 418 | EP-A-164 597 |
| EP-A 120 515 | EP-A-175 966 |
| EP-A-120 516 | WO 84/02913 |
| EP-A-172 112 | WO 84/02919 |
| EP-A-140 556 | WO 84/02920 |
| EP-A-174 166 | WO 83/01176 |
| EP-A-122 791 | |
| EP-A-0 309 862 | |
| EP-A-0 464 461 | |
| EP-A-0 533 010 | |

We claim:

1. DNA sequence I, which comprises the following components sequentially ordered in the 5'-3' direction:
   a) a promoter, which is heterologous in relation to component b), which is strongly active in plants or which is anther-specific or tapetum-specific, and which is, optionally, located downstream of an enhancer;
   b) a DNA sequence encoding stilbene synthase; and
   c) a 3' polyadenylation sequence.

2. DNA sequence I according to claim 1, where component a) comprises a plant virus promoter and, optionally, an enhancer.

3. DNA sequence I according to claim 1, where component a) comprises an anther-specific or tapetum-specific promoter.

4. DNA sequence I according to claim 1, where component a) comprises the CaMV 35S promoter.

5. DNA sequence I according to claim 1, where component a) comprises the CaMV 35S promoter placed downstream of the CaMV 35S enhancer.

6. DNA sequence I according to claim 1, where component a) comprises the construct consisting of the CaMV 35S promoter and the CaMV 35S enhancer which is present on plasmid pSSVst1.

7. DNA sequence I according to claim 1, where component a) comprises the construct consisting of nucleotides 1 to 720 of SEQ ID NO: 7.

8. DNA sequence I according to claim 1, in which component b) comprises a resveratrol synthase-encoding DNA sequence.

9. DNA sequence I according to claim 1, in which component b) comprises a resveratrol synthase-encoding DNA sequence from *Arachis hypogea* or *Vitis vinifera* or a cDNA of said resveratrol synthase-encoding DNA sequence from *Arachis hypogea* or *Vitis vinifera*.

10. DNA sequence I according to claim 1, in which component b) comprises a resveratrol synthase-encoding DNA sequence from *Vitis vinifera* or a cDNA of said resveratrol synthase-encoding DNA sequence from *Vitis vinifera*.

11. DNA sequence I according to claim 1, in which component b) comprises the resveratrol synthase-encoding DNA sequence which is present on plasmid pSSVst1.

12. DNA sequence I according to claim 1, in which component b) comprises the resveratrol synthase-encoding DNA sequence which consists of nucleotides 731 to 2265 according to SEQ ID NO: 7.

13. DNA sequence I according to claim 1, in which component c) comprises a 3' polyadenylation sequence which is present in a natural stilbene synthase gene.

14. DNA sequence I according to claim 1, in which component c) comprises the 3' polyadenylation sequence which is present in plasmid pSSVst1.

15. DNA sequence I according to claim 1, in which component c) comprises the 3' polyadenylation sequence which consists of nucleotides 2266 to 2485 or 2266 to 2728 according to SEQ ID NO: 7.

16. DNA sequence I according to claim 1, which consists of the combination of components a) to c).

17. DNA sequence I according to claim 1, which consists of nucleotides 1 to 2728 according to SEQ NO: 7.

18. Recombinant prokaryotic or eukaryotic DNA which comprises the DNA sequence I according to claim 1.

19. Recombinant plant DNA which comprises the DNA sequence I according to claim 1.

20. A vector which comprises the DNA sequence I according to claim 1.

21. Vector according to claim 20, which is plasmid pSSVst1.

22. A microorganism which comprises the DNA sequence I according to claim 1.

23. Microorganism according to claim 22, which is *Escherichia coli* strain RH pSSVst1 (according to DSM 9501), or a mutant thereof which comprises pSSVst1.

24. A transgenic plant which comprises the DNA sequence I according to claim 1 in its genome and which is male-sterile or exhibits a flower color which is altered as compared with a plant of the same species which does not comprise the DNA sequence I, or a part of said transgenic plant.

25. A transgenic plant according to claim 24, which comprises, as DNA sequence I, the DNA sequence I which is present on plasmid pSSVst1, or a part of said transgenic plant.

26. A transgenic plant according to claim 24, which comprises, as DNA sequence I, the DNA sequence I which consists of nucjeotides 1 to 2728 according to SEQ ID NO: 7, or a part of said transgenic plant.

27. Process for preparing transgenic plant cells and optionally transgenic plants, said process comprising:
(a) inserting the DNA sequence I according to claim 1 into the genome of plant cells to yield transgenic plant cells comprising DNA sequence I and, optionally,
(b) regenerating said transgenic plant cells to yield a parental generation of complete, transgenic plants and, optionally,
(c) replicating said transformed plants to yield other generations of transgenic plants, and, optionally,
(d) isolating desired plant parts from said transgenic plants of said parental generation or said other generations.

28. A vector which comprises the recombinant DNA according to claim 18.

29. A microorganism which comprises the recombinant DNA according to claim 18.

30. Process for preparing transgenic plant cells and optionally transgenic plants, said process comprising:
(a) inserting the recombinant DNA according to claim 18 into the genome of plant cells to yield transgenic plant cells comprising DNA sequence I and, optionally,
(b) regenerating said transgenic plant cells to yield a parental generation of complete, transgenic plants and, optionally,
(c) replicating said transformed plants to yield other generations of transgenic plants, and, optionally,
(d) isolating desired plant parts from said transgenic plants of said parental generation or said other generations.

31. A transgenic plant or part according to claim 24, which is a transgenic protoplast, plant cell, callus, seed, tuber or cutting.

32. Process according to claim 27, wherein the plant cells are protoplasts.

33. Process according to claim 30, wherein the plant cells are protoplasts.

34. DNA sequence I, which comprises the following components sequentially ordered in the 5'-3' direction:
a) a promoter, which is heterologous in relation to component b), which is strongly active in plants or which is anther-specific or tapetum-specific, and which is, optionally, located downstream of an enhancer;
b) a DNA sequence encoding stilbene synthase; and
c) a 3' polyadenylation sequence;

said DNA sequence I, when introduced into the genome of a plant and expressed therein, conferring on said plant male-sterility or a flower color which is altered as compared to a plant of the same species which does not comprise the DNA sequence I.

* * * * *

UNITED STATES PATENT AND TRADEMARK OFFICE
CERTIFICATE OF CORRECTION

PATENT NO.     : 6,063,988
DATED          : May 16, 2000
INVENTOR(S)    : Rudiger Hain et al.

It is certified that error appears in the above-identified patent and that said Letters Patent is hereby corrected as shown below:

Column 23,
Line 1, change "nucjeotides" to -- nucleotides --

Signed and Sealed this

Ninth Day of September, 2003

JAMES E. ROGAN
*Director of the United States Patent and Trademark Office*

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (xi) SEQUENCE DESCRIPTION: SEQ ID NO: 1:

TCCCCCGGGA TCCATGGCTT CAATTGAGGA AAT                33

(2) INFORMATION FOR SEQ ID NO: 2:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (xi) SEQUENCE DESCRIPTION: SEQ ID NO: 2:

TCCCCCGGGA TCCATGGCGT CTGTGGAGGA AAT                33

(2) INFORMATION FOR SEQ ID NO: 3:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (xi) SEQUENCE DESCRIPTION: SEQ ID NO: 3:

TCCCCCGGGA TCCATGGTGT CTGTGAGTGG AAT                33

(2) INFORMATION FOR SEQ ID NO: 4:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (xi) SEQUENCE DESCRIPTION: SEQ ID NO: 4:

TGAATTCCCG GGTCAATTTG TAACCATAGG AA                 32

(2) INFORMATION FOR SEQ ID NO: 5:

(i) SEQUENCE CHARACTERISTICS:

(A) LENGTH: 31 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 5:

CGGATCCCGG GTCAATTGGA ATCCCTAGGA A                          31

(2) INFORMATION FOR SEQ ID NO: 6:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 6:

CGGATCCCGG GTCTTCGCAT AACGAATTAA CT                         32

(2) INFORMATION FOR SEQ ID NO: 7:

(i) SEQUENCE CHARACTERISTICS:
            (A) LENGTH: 2728 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO: 7:

AAGCTTGCAT GCCTGCAGGT CTCAGAAGAC CAGAGGGCTA                  40

TTGAGACTTT TCAACAAAGG GTAATATCGG GAAACCTCCT                  80

CGGATTCCAT TGCCCAGCTA TCTGTCACTT CATCGAAAGG                 120

ACAGTAGAAA AGGAAGATGG CTTCTACAAA TGCCATCATT                 160

GCGATAAAGG AAAGGCTATC GTTCAAGAAT GCCTCTACCG                 200

ACAGTGGTCC CAAAGATGGA CCCCCACCCA CGAGGAACAT                 240

CGTGGAAAAA GAAGACGTTC CAACCACGTC TTCAAAGCAA                 280

GTGGATTGAT GTGATAACAT GGTGGAGCAC GACACTCTCG                 320

TCTACTCCAA GAATATCAAA GATACAGTCT CAGAAGACCA                 360

GAGGGCTATT GAGACTTTTC AACAAAGGGT AATATCGGGA                 400

AACCTCCTCG GATTCCATTG CCCAGCTATC TGTCACTTCA                 440

TCGAAAGGAC AGTAGAAAAG GAAGATGGCT TCTACAAATG                 480

CCATCATTGC GATAAAGGAA AGGCTATCGT TCAAGAATGC                 520

CTCTACCGAC AGTGGTCCCA AAGATGGACC CCCACCCACG                 560

AGGAACATCG TGGAAAAAGA AGACGTTCCA ACCACGTCTT                 600

CAAAGCAAGT GGATTGATGT GATATCTCCA CTGACGTAAG                 640

GGATGACGCA CAATCCCACT ATCCTTCGCA AGACCCGTCC                 680

-continued

| | |
|---|---|
| TCTATATAAG GAAGTTCATT TCATTTGGAG AGGACCTCGA | 720 |
| GAATTCCACC ATGGCTTCAA TTGAGGAAAT TAGAAACGCT | 760 |
| CAACGTGCCA AGGGTCCGGC CACCATCCTA GCCATTGGCA | 800 |
| CAGCTACTCC CGACCACTGT GTCTACCAGT CTGATTATGC | 840 |
| TGATTACTAT TTCAGAGTCA CTAAGAGCGA GCACATGACT | 880 |
| GAGTTGAAGA AGAAGTTCAA TCGCATATGT AAGTATATAT | 920 |
| ATTCATGCAT TAATTCTTAC ATTCACAACA TTTCTATACA | 960 |
| TATACGAGTG TGCTATTAAG TGAGGGTCAC CTCCAAGTGA | 1000 |
| ATGAATGTTT CAAGCTTAGA GAATAGCTTT TAGCTAAATT | 1040 |
| ACTTTAGGAA ACTTGAAAAT CATTTTACAT CAGTAACCGA | 1080 |
| TATTCCTTTC ATTTGATTGT AAGGGCTTGA AGAGCTGTTC | 1120 |
| TTTGAATCAT GTAGCATTGC TAGCTATAAT TAAGAATAAC | 1160 |
| CTTTTATAAT TTCTTCAATG TTAAATGCAT GTTGATCATC | 1200 |
| TTCAAGAATA TACTATATGA CTAGTCGTTG GAAAACTAAT | 1240 |
| GTGTTCATCT TATTTCTTTT ACAGGTGACA AATCAATGAT | 1280 |
| CAAGAAGCGT TACATTCATT TGACCGAAGA AATGCTTGAG | 1320 |
| GAGCACCCAA ACATTGGTGC TTATATGGCT CCATCTCTCA | 1360 |
| ACATACGCCA AGAGATTATC ACTGCTGAGG TACCTAAACT | 1400 |
| TGGTAAAGAA GCAGCATTGA AGGCTCTTAA AGAATGGGGT | 1440 |
| CAACCAAAGT CCAAGATCAC CCATCTTGTA TTTTGTACAA | 1480 |
| CCTCCGGTGT AGAAATGCCC GGTGCAGATT ACAAACTCGC | 1520 |
| TAATCTCTTA GGCCTTGAAA CATCGGTTAG AAGGGTGATC | 1560 |
| TTGTACCATC AAGGTTGCTA TGCAGGTGGA ACTGTCCTTC | 1600 |
| GAACTGCTAA GGATCTTGCA GAAAATAACG CAGGAGCACG | 1640 |
| AGTTCTTGTG GTGTGCTCTG AGATCACTGT TGTTACATTT | 1680 |
| CGTGGGCCTT CCGAAGATGC TTTGGACTCT TTAGTAGGTC | 1720 |
| AAGCCCTTTT TGGTGATGGG TCAGCAGCTG TGATTGTTGG | 1760 |
| ATCAGATCCA GATGTCTCCA TTGAACGACC CCTCTTCCAA | 1800 |
| CTTGTTTCAG CAGCACAAAC GTTTATTCCT AATTCAGCAG | 1840 |
| GTGCTATTGC GGGTAACTTA CGTGAGGTGG GACTCACCTT | 1880 |
| TCACTTGTGG CCTAATGTGC CTACTTTGAT TTCCGAGAAC | 1920 |
| ATAGAGAAAT GCTTGAATCA GGCTTTTGAC CCACTTGGTA | 1960 |
| TTAGCGATTG GAACTCGTTA TTTTGGATTG CTCACCCTGG | 2000 |
| TGGCCCTGCA ATTCTTGATG CAGTTGAAGC AAAACTCAAT | 2040 |
| TTAGAGAAAA AGAAACTTGA AGCAACAAGG CATGTGTTAA | 2080 |
| GTGAGTATGG TAACATGTCT AGTGCATGTG TCTTGTTTAT | 2120 |
| TTTGGATGAG ATGAGAAAGA AATCCCTAAA GGGGGAAAAA | 2160 |
| GCTACCACAG GTGACGGATT GGATTGGGGN GTACTATTCG | 2200 |
| GTTTTGGGCC AGGCTTGACC ATTGAGACCG TTGTGCTGCA | 2240 |
| TAGCGTTCCT ATGGTTACAA ATTGAGTGGA AAACGGTAAG | 2280 |

```
AGAAATGATA TAGGGGACAT GTCTTATTGT ATTACAGAGG                      2320

AGGTGCTACG AAAGATATGT ACATGTATCT TCAAAGTTAA                      2360

TAATAGTACT CCTAAATCTT TTATTCCTAT CCTAACATTG                      2400

AGGGATTGTA ATTTAGTGAT TGTTGGAGGG TGCAGTCACG                      2440

TCAGGCAAGT GGATGAAACT GCAAGTGCTT GTCATTCTGT                      2480

TATCGGGGGA TCCTCTAGAG TCCGCAAAAA TCACCAGTCT                      2520

CTCTCTACAA ATCTATCTCT CTCTATTTTT CTCCAGAATA                      2560

ATGTGTGAGT AGTTCCCAGA TAAGGGAATT AGGGTTCTTA                      2600

TAGGGTTTCG CTCATGTGTT GAGCATATAA GAAACCCTTA                      2640

GTATGTATTT GTATTTGTAA AATACTTCTA TCAATAAAAT                      2680

TTCTAATTCC TAAAACCAAA ATCCAGTGAC CTGCAGGCAT                      2720

GCAAGCTT                                                         2728
```